April 25, 1972
M. N. ROBINSON
Plant Pat. 3,136
DWARF BOSTON FERN PLANT
Filed Aug. 1, 1969
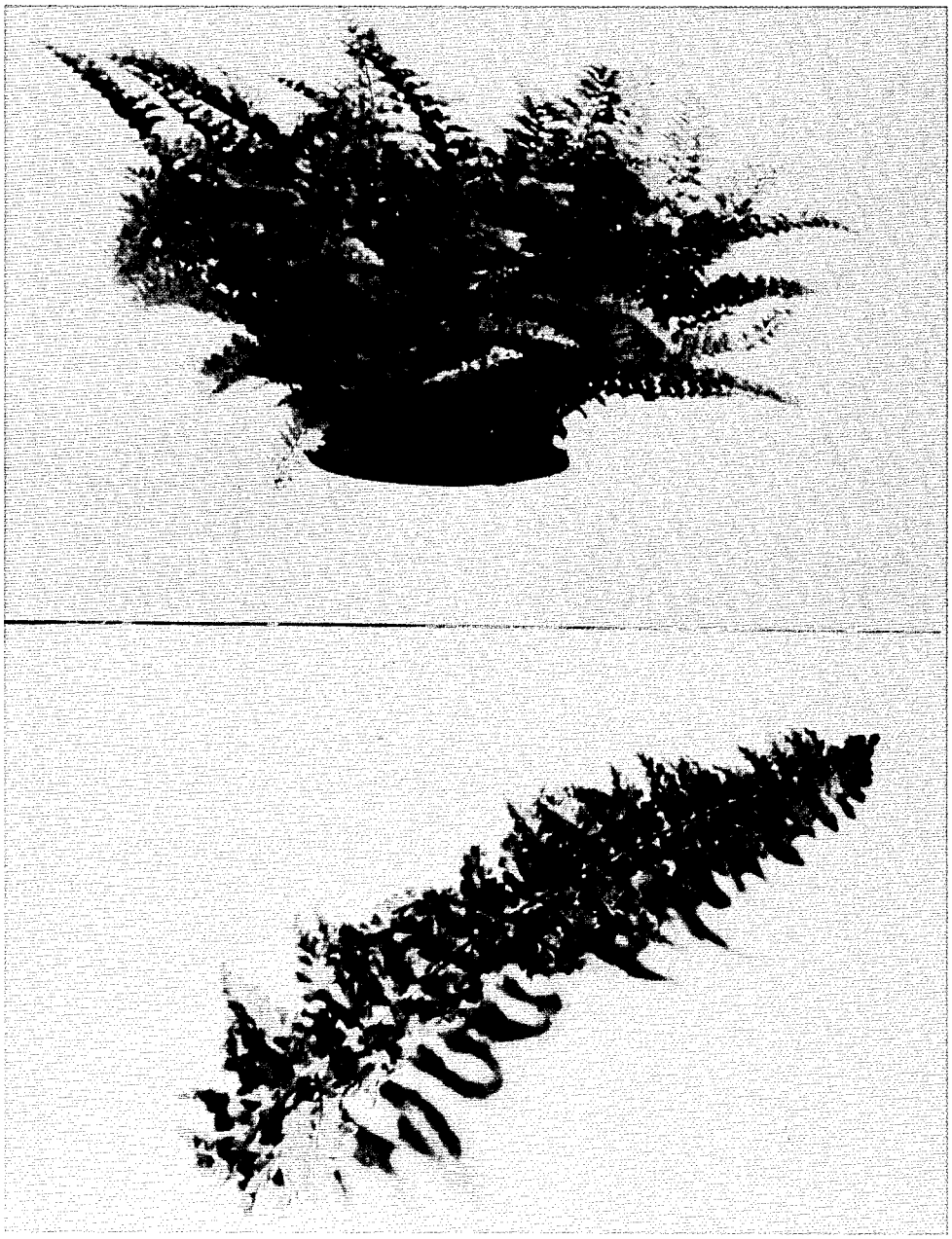
INVENTOR
MERCHANT NEAL ROBINSON,
By
Berman, Davidson & Berman,
ATTORNEYS.

United States Patent Office

Plant Pat. 3,136
Patented Apr. 25, 1972

3,136

DWARF BOSTON FERN PLANT

Merchant Neal Robinson, Brownsville, Tex.; Don M. Robinson, executor, Brownsville, Tex.

Filed Aug. 1, 1969, Ser. No. 846,982
Int. Cl. A01h *9/00*
U.S. Cl. Plt.—88 1 Claim

The present invention relates to a new and distinct variety of Boston fern, which was discovered by me in my greenhouses located at Brownsville, Tex., as a sport of the widely grown variety known as "Fluffy Ruffles" (unpatented), which is a variety of the species botanically known as *Nephrolepsis exaltata.*

At the time of my discovery, I was commercially growing plants of the variety "Fluffy Ruffles" in my greenhouses aforementioned, and during my growing operations, my attention was attracted to one particular plant among those which generally resembled the other plants in substantially all respects except that it was very small in size in comparison with the other plants. Upon close inspection of the small plant, I found that one plant of "Fluffy Ruffles" apparently had sported, and I thereupon took steps to carefully preserve the sport and keep it under close and continuous observation. On finding that it retained its dwarf size, while all the other plants of "Fluffy Ruffles" continued their normal growth, I extensively reproduced the sport by division of the original growth and of subsequent progeny derived therefrom, as performed by me in my greenhouses aforesaid. From observations of several hundred plants so reproduced, I found that there was no evidence whatsoever of either reversion to the parent plant characteristics or any change in growth habit. I therefore concluded that my new sport is a true clon and basically differs from all other known clons or sports of Nephrolepsis, as evidenced by the fact that none of the plants derived from this sport have ever exceeded an overall spread greater than seven inches, or a height greater than seven inches, or a height greater than three and one-half inches.

All ferns of the genus Nephrolepsis are tenacious of life and will withstand some adverse conditions. Consequently, *Nephrolepsis exaltata* and its cultivars are presently in use quite widely as house plants and for indoor or outdoor landscape plantings. One of the cultivars of this genus grown most widely in recent years is the *Nephrolepsis exaltata* "Fluffy Ruffles," which is the parent of my new sport. It is therefore a commercially valuable asset to be able to more or less duplicate such plants in miniature or dwarf form as achieved by my new discovery.

The accompanying drawing shows a typical specimen plant of my new variety, together with a typical frond thereof shown on a somewhat enlarged scale, all as depicted in color as nearly true as it is reasonably possible to make the same in a color illustration of this character.

The following is a detailed description of my new dwarf fern variety, with color terminology in accordance with Nickerson's Color Fan, published by Munsell Color Company, Inc., of Baltimore, Md., except where general color terms of ordinary dictionary significance are obvious:

Plant:

*Growth habit.*—Rapid; mature height of plant develops rather quickly and then begins to develop thick, compact lateral growth without any additional frond length; dwarf; well-shaped; maximum spread about 7 inches; maximum height about 3½ inches.

*Fronds.*—Stiff; upright; slightly recurving; pinnate when young, but tightly bi-pinnate when mature, with crenate margins on both the leaflets and the pinnae; usually about 3 inches long or slightly less. Color—Rich green, near Moderate Olive Green, Hue 7.5 GY 4/4.

*Pinnae.*—When present are from 1/16 inch to 1/8 inch long.

*Leaflets.*—Average from ½ inch to ¾ inch long.

Stolons (runners): Not characteristic of this variety, but when present, they are extremely short and modified.

Crown: Compact; develops natural stools or divisions with from 8 to 12 fronds per division and from 20 to 25 divisions in a plant of 3 inches in diameter.

Propagation: Holds its distinguishing characteristics by natural seperations of the compact crown.

I claim:

1. A new and distinct variety of Boston fern, substantially as herein shown and described, characterized particularly as to novelty by its general resemblance to the *Nephrolepsis exaltata* "Fluffy Ruffles" (unpatented) from which it sported, except for its distinctive dwarf size which usually averages less than 3 inches in height, a well shaped and compact plant habit, a rich green frond color, with the fronds being upright, stiff and pinnate when young, but tightly bi-pinnate when mature and having crenate margins on both the leaflets and the pinnae, said fronds attaining their mature height relatively quickly and then filling out laterally without increasing in height, and a compact crown which develops natural stools or divisions which are easily separable for propagation purposes.

No references cited.

ROBERT E. BAGWILL, Primary Examiner

UNITED STATES PATENT OFFICE

CERTIFICATE OF CORRECTION

Patent No. Plant 3,136 Dated April 25, 1972

Inventor(s) Merchant Neal Robinson

It is certified that error appears in the above-identified patent and that said Letters Patent are hereby corrected as shown below:

Column 1, lines 38 and 39 cancel "or a height greater than seven inches,". Column 2, line 34 "seperations" should read -- separations --.

Signed and sealed this 7th day of November 1972.

(SEAL)
Attest:

EDWARD M.FLETCHER,JR.
Attesting Officer

ROBERT GOTTSCHALK
Commissioner of Patents

USCOMM-DC 60376-P69
U.S. GOVERNMENT PRINTING OFFICE : 1969 O—366-334